United States Patent [19]
Cotteret

[11] Patent Number: 6,024,769
[45] Date of Patent: *Feb. 15, 2000

[54] PROCESS FOR DYEING KERATINOUS FIBRES WITH AN ALKOXYMETAPHENYLENEDIAMINE AT ACIDIC PH AND COMPOSITIONS USED

[75] Inventor: Jean Cotteret, Verneuil-sur-Seine, France

[73] Assignee: L'Oreal, Paris, France

[ * ] Notice: This patent issued on a continued prosecution application filed under 37 CFR 1.53(d), and is subject to the twenty year patent term provisions of 35 U.S.C. 154(a)(2).
This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/479,203

[22] Filed: Jun. 7, 1995

Related U.S. Application Data

[63] Continuation of application No. 08/244,319, filed as application No. PCT/FR92/01115, Dec. 1, 1992, abandoned.

[30] Foreign Application Priority Data

Dec. 3, 1991 [FR] France .................. 91 14947

[51] Int. Cl.$^7$ .................................. A61K 7/13
[52] U.S. Cl. ........................ 8/411; 8/408; 8/416
[58] Field of Search ............... 8/406, 408, 410, 8/411, 412, 416, 409

[56] References Cited

U.S. PATENT DOCUMENTS

| | | | |
|---|---|---|---|
| 3,649,159 | 3/1972 | Cohen et al. | 8/10.2 |
| 3,977,826 | 8/1976 | Iscowitz | 8/10.2 |
| 3,986,825 | 10/1976 | Sokol | 8/406 |
| 4,125,367 | 11/1978 | Bugaut et al. | 8/411 |
| 4,226,595 | 10/1980 | Rose et al. | 8/406 |
| 4,323,360 | 4/1982 | Bugaut et al. | 8/411 |
| 4,330,292 | 5/1982 | Bugaut et al. | 8/411 |
| 4,348,202 | 9/1982 | Grollier et al. | 8/406 |
| 4,357,141 | 11/1982 | Grollier et al. | 8/406 |
| 4,425,132 | 1/1984 | Grollier et al. | 8/406 |
| 4,566,876 | 1/1986 | Brown et al. | 8/411 |
| 4,854,935 | 8/1989 | Clausen et al. | 8/408 |
| 4,865,619 | 9/1989 | Junino et al. | 8/411 |
| 4,891,045 | 1/1990 | Junino et al. | 8/411 |
| 4,960,432 | 10/1990 | Junino et al. | 8/411 |
| 4,970,066 | 11/1990 | Grollier et al. | 8/406 |
| 4,985,955 | 1/1991 | Grollier et al. | 8/406 |
| 5,002,585 | 3/1991 | Junino et al. | 8/411 |
| 5,180,397 | 1/1993 | Grollier et al. | 8/406 |
| 5,500,021 | 3/1996 | Cotteret et al. | 8/408 |
| 5,500,022 | 3/1996 | Cotteret | 8/410 |
| 5,518,507 | 5/1996 | Audousset et al. | 8/411 |
| 5,690,696 | 11/1997 | Bone et al. | 8/411 |

FOREIGN PATENT DOCUMENTS

| | | |
|---|---|---|
| 0 002 828 | 7/1979 | European Pat. Off. . |
| 0 029 964 | 6/1981 | European Pat. Off. . |
| 0 459 900 | 12/1991 | European Pat. Off. . |
| 2758735 | 4/1979 | Germany . |
| 2 942 297 | 5/1981 | Germany . |
| 3 007 997 | 9/1981 | Germany . |
| 1597034 | 9/1981 | United Kingdom . |
| 2 216 124 | 10/1989 | United Kingdom . |
| WO88/00042 | 1/1988 | WIPO . |

*Primary Examiner*—Caroline D. Liott
*Attorney, Agent, or Firm*—Jacobson, Price, Holman, Stern, PLLC

[57] ABSTRACT

Dyeing keratinous fibers, in particular human keratinous fibers such as hair, by applying to these fibers a composition containing, in a medium suitable for dyeing at least, as coupler, one alkoxymethaphenylenediamine of formula (I) below:

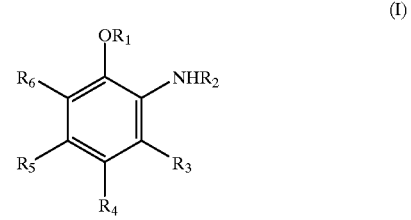

(I)

which is, for example, 2,4-diaminoanisole, and at least one oxidation dye precursor or oxidation base, at least one oxidizing agent, wherein the pH of the composition applied to the fibers is less than 7.

25 Claims, No Drawings

PROCESS FOR DYEING KERATINOUS FIBRES WITH AN ALKOXYMETAPHENYLENEDIAMINE AT ACIDIC PH AND COMPOSITIONS USED

This is a continuation of application Ser. No. 08/244,319, filed Aug. 12, 1994, now abandoned, which is a 371 of International Application PCT/FR92/01115, which has an international filing date of Dec. 1, 1992.

The present invention relates to a new process for dyeing keratinous fibres, in particular human keratinous fibres such as hair, using an alkoxymetaphenylenediamine in combination with oxidation bases and an oxidising agent, in an acidic medium, and to the compositions used during this process.

The dyeing of keratinous fibres, and in particular human hair, with dyeing compositions containing, in alkaline medium, oxidation dye precursors, and in particular p-phenylenediamines, ortho- or para-aminophenols generally called "oxidation bases", is known.

It is also known that it is possible to vary the shades obtained with these oxidation bases by combining them with couplers also called colour modifiers, which are chosen in particular from aromatic meta-diamines, meta-aminophenols and meta-diphenols.

Moreover, the production of warm hues is difficult in the case of oxidation dyeing at acidic pH.

The Applicant has just discovered that the use of alkoxymetaphenylenediamines, which are defined below, with oxidation bases, in a freshly prepared mixture with an oxidant, at an acidic pH, made it possible to obtain barely selective dyes, that is to say that their colour is essentially the same on natural hair and on sensitised hair, having good resistance to light, to washings, to perspiration and to adverse weather conditions.

The subject of the present invention is therefore a process for dyeing keratinous fibres, in particular human keratinous fibres such as hair, comprising the application to these fibres of at least one composition containing an alkoxymetaphenylenediamine of formula (I), one oxidation dye precursor also called oxidation base and one oxidising agent, at acidic pH.

The subject of the invention is also a dyeing agent containing two components, one of the components of which comprises the alkoxymetaphenylenediamine of formula (I) below and the oxidation dye precursor, and the other the oxidising agent, at an acidic pH, and in amounts such that the mixture has an acidic pH.

The subject of the invention is also the ready-for-use composition containing the different agents used for dyeing hair in acidic medium.

Other subjects of the invention will become apparent on reading the description and examples below.

The process for dyeing keratinous fibres, and in particular human keratinous fibres such as hair, conforming to the invention, is essentially characterised in that there is applied to these fibres a composition containing, in a-medium suitable for dyeing:

at least, as coupler, one alkoxymetaphenylenediamine of formula (I) below:

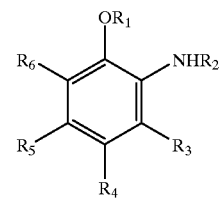

in which:

$R_1$ represents a $C_1$–$C_4$-alkyl radical, a $C_2$–$C_4$ mono- or polyhydroxyalkyl radical, a $C_1$–$C_4$-carboxyalkyl radical or a $C_1$–$C_4$-aminoalkyl radical whose amino group may be mono- or disubstituted by a $C_1$–$C_4$-alkyl;

$R_2$ represents a hydrogen atom, a $C_1$–$C_4$-alkyl radical, a $C_2$–$C_4$ mono- or polyhydroxyalkyl radical;

$R_3$ and $R_5$, independently of each other, represent H or OR, R denoting a $C_1$–$C_4$-alkyl radical or a $C_2$–$C_4$ mono- or polyhydroxyalkyl radical;

$R_4$ represents a hydrogen atom, a $C_1$–$C_4$-alkyl radical or NHR';

$R_6$ represents a hydrogen atom, a $C_1$–$C_4$-alkyl radical, OR or NHR', R having the meaning given above;

R' denotes a hydrogen atom, a $C_1$–$C_4$-alkyl radical or a $C_2$–$C_4$ mono- or polyhydroxyalkyl radical; provided that:

a) one and only one of the radicals $R_4$ and $R_6$ denotes NHR';

b) $R_3$ and $OR_1$ cannot simultaneously denote methoxy hen $R_2$, $R_5$ and $R_6$ simultaneously denote hydrogen and $R_4$ the $NH_2$ group;

c) at least one of the radicals $R_3$, $R_4$, $R_5$ or $R_6$ denotes H;

d) $R_3$, $R_4$ and $R_5$ cannot simultaneously denote hydrogen when $R_6$ denotes $NH_2$, $R_2$ denotes hydrogen and $R_1$ denotes methyl;

e) when $R_1$ denotes ethyl and $R_2$, $R_3$, $R_5$ and $R_6$ denote H, $R_4$ cannot denote $NH_2$;

f) $R_4$ must represent NHR' when $R_1$ denotes carboxyalkyl or aminoalkyl;

as well as the salts of these compounds;

at least one oxidation dye precursor or oxidation base;

at least one oxidising agent;

the pH of the composition applied to the fibres being less than 7.

The composition does not contain iodide ions in sufficient quantity to oxidise the alkoxymetaphenylenediamine of formula (I).

The salts are chosen from the addition salts of acids such as hydrochloric, hydrobromic and sulphuric acids and the like.

By way of compounds of formula (I), there may be mentioned:

2,4-diaminoanisole,
2-N-β-hydroxyethylamino-4-amino-1,3,5-trimethoxybenzene,
2-N-β-hydroxyethylamino-4-amino-1-methoxybenzene,
4-N-β-hydroxyethylamino-2-amino-1-methoxybenzene,
2,4-diamino-1,5-dimethoxybenzene,
2,4-di-(β-hydroxyethylamino)-1-methoxybenzene,
2,4-diamino-5-methoxyphenoxyethanol,
2,4-diamino-1,3,5-trimethoxybenzene, 2,4-diamino-1,5-di-(β-hydroxyethoxy)benzene,
2,4-diaminophenoxyethanol,
2,4-diamino-6-methyl-1-methoxybenzene,
2,4-diamino-1,6-dimethoxybenzene,
2,6-diamino-4-methyl-1-methoxybenzene,
as well as their salts.

The oxidation dye precursors or oxidation bases are known compounds which are not dyes themselves and which form a dye by a process of oxidative condensation either with themselves or in the presence of a coupler or modifier. These compounds generally contain an aromatic ring carrying functional groups, consisting: either of two amino groups, or of an amino group and a hydroxyl group; these groups being in the para or ortho position relative to each other.

The para type oxidation dye precursors used in conformity with the invention are chosen from para-phenylenediamines, para-aminophenols, para heterocyclic precursors such as 2,5-diaminopyridine, 2-hydroxy-5-aminopyridine and 2,4,5,6-tetraaminopyrimidine.

The para-aminophenols are particularly useful for producing warm shades (red and copper-coloured).

Among the para-phenylenediamines, there may be mentioned the compounds of formula (II):

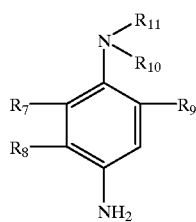

(II)

in which:
R$_7$, R$_8$ and R$_9$, which are identical or different, represent a hydrogen or halogen atom, an alkyl radical having 1 to 4 carbon atoms, an alkoxy radical having 1 to 4 carbon atoms;

R$_{10}$ and R$_{11}$, which are identical or different, represent a hydrogen atom, an alkyl, hydroxyalkyl, alkoxyalkyl, carbamylalkyl, mesylaminoalkyl, acetylaminoalkyl, ureidoalkyl, carbalkoxyaminoalkyl, sulphoalkyl, piperidinoalkyl or morpholinoalkyl radical; these alkyl or alkoxy groups having 1 to 4 carbon atoms, or alternatively R$_{10}$ and R$_{11}$ form, together with the nitrogen atom to which they are attached, a piperidino or morpholino heterocycle, provided that R$_7$ or R$_9$ represents a hydrogen atom when R$_{10}$ and R$_{11}$ do not represent a hydrogen atom, as well as the salts of these compounds excluding 2,6-dimethylparaphenylenediamine and 2,3-dimethylparaphenylenediamine.

In the formulae (I) and (II) above, by way of alkyl radicals, there may be mentioned: methyl, ethyl, propyl, isopropyl, butyl and isobutyl; by way of monohydroxyalkyl radicals, there may be mentioned β-hydroxyethyl, β-hydroxypropyl, γ-hydroxypropyl; by way of polyhydroxyalkyl radical, there may be mentioned β,γ-dihydroxypropyl.

Among the preferred compounds of formula (II) there may be mentioned isopropyl-p-phenylenediamine, p-phenylenediamine, 2-methyl-p-phenylenediamine, methoxyparaphenylenediamine, chloroparaphenylenediamine, 2-methyl-5-methoxyparaphenylenediamine, 2,6-dimethyl-5-methoxyparaphenylenediamine, N,N-dimethylparaphenylenediamine, 3-methyl-4-amino-N,N-diethylaniline, N,N-di-(β-hydroxyethyl)paraphenylenediamine, 3-methyl-4-amino-N,N-di-(β-hydroxyethyl)aniline, 3-chloro-4-amino-N,N-di-(β-hydroxyethyl)aniline, 4-amino-N,N-(ethylcarbamylmethyl)aniline, 3-methyl-4-amino-N,N-(ethylcarbamylmethyl)aniline, 4-amino-N,N-(ethyl-β-piperidinoethyl)aniline, 3-methyl-4-amino-N,N-(ethyl-β-piperidinoethyl)aniline, 4-amino-N,N-(ethyl-β-morpholinoethyl)aniline, 3-methyl-4-amino-N,N-(ethyl-β-morpholinoethyl)aniline, 4-amino-N,N-(ethyl-β-acetylaminoethyl)aniline, 4-amino-N-(β-methoxyethyl)aniline, 3-methyl-4-amino-N,N-(ethyl-β-acetylaminoethyl)aniline, 4-amino-N,N-(ethyl-β-mesylaminoethyl)aniline, 3-methyl-4-amino-N,N-(ethyl-β-mesylaminoethyl)aniline, 4-amino-N,N-(ethyl-β-sulphoethyl)aniline, 3-methyl-4-amino-N,N-(ethyl-β-sulphoethyl)aniline, N-[(4'-amino)phenyl]morpholine and N-[(4'-amino)phenyl]piperidine.

These para type oxidation dye precursors may be introduced in the dyeing composition in the form of the free base or in the form of salts such as in hydrochloride, hydrobromide or sulphate form.

Among the p-aminophenols, there may be mentioned p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2-hydroxymethyl-4-aminophenol, 2-(β-hydroxyethyl)-4-aminophenol, 2-methoxy-4-aminophenol, 3-methoxy-4-aminophenol, 2,5-dimethyl-4-aminophenol, 2-methoxymethyl-4-aminophenol, 2-aminomethyl-4-aminophenol, 2-β-hydroxyethylaminomethyl-4-aminophenol, 2-ethoxymethyl-4-aminophenol, 2-(β-hydroxyethoxy)methyl-4-aminophenol, N-(2-hydroxy-5-aminobenzyl)-2-methoxyethylamine, N-(2-hydroxy-5-aminobenzyl)-1-methoxyisopropylamine, N-(2-hydroxy-5-aminobenzyl)-3-isopropoxypropylamine, 2-acetylamino-4-aminophenol or 5-aminosalicylic acid.

The ortho type oxidation dye precursors are chosen from ortho-aminophenols such as 1-amino-2-hydroxybenzene, 6-methyl-1-hydroxy-2-aminobenzene, 4-methyl-1-amino-2-hydroxybenzene and ortho-phenylenediamines.

The oxidising agent is preferably chosen from hydrogen peroxide, urea peroxide, alkali metal bromates, persalts such as perborates and persulphates. Hydrogen peroxide is particularly preferred.

The pH of the composition applied to the keratinous fibres, in particular hair, has a value of less than 7 and is preferably between 3 and 6.9. This pH is adjusted using acidifying agents which are well known in the field relating to the dyeing of keratinous fibres, and in particular human hair, such as inorganic or organic acids such as hydrochloric acid, phosphoric acid, carboxylic acids such as tartaric acid, citric acid or sulphonic acids.

The alkoxymetaphenylenediamine of formula (I) is present in the composition applied to the keratinous fibres, in proportions preferably of between 0.01 and 3.5% by weight relative to the total weight of the composition.

The above-defined compositions, applied in the dyeing of keratinous fibres, may also contain, in addition to the alkoxymetaphenylenediamine of formula (I), other couplers which are known per se, such as meta-diphenols, meta-aminophenols, meta-phenylenediamines, meta-N-acylaminophenols, meta-ureidophenols, meta-carbalkoxyaminophenols, α-naphthol, indole couplers, couplers possessing an active methylene group, such as diketonic compounds and pyrazolones, excluding 2,4-diamino-1,3-dimethoxybenzene.

Among these couplers which can be used in addition to the alkoxymetaphenylenediamine of formula (I), there may be mentioned 2,4-dihydroxyphenoxyethanol, 2,4-dihydroxyanisole, meta-aminophenol, resorcinol, resorcinol monomethyl ether, 2-methylresorcinol, pyrocatechol, 2-methyl-5-N-(β-hydroxyethyl)aminophenol, 2-methyl-5-N-(β-mesylaminoethyl)aminophenol, 6-hydroxybenzomorpholine, 6-aminobenzomorpholine, 2,4-diaminophenoxyethylamine, 2-methyl-5-aminophenol, 2,6-dimethyl-3-aminophenol, 3,4-methylenedioxyphenol, 3,4-methylenedioxyaniline, 4-hydroxyindole, 6-hydroxyindole, 7-hydroxyindole, 7-aminoindole and their salts.

These compositions may also contain anionic, cationic, nonionic, or amphoteric surface-active agents or mixtures thereof.

Among these surface-active agents, there may be mentioned alkylbenzenesulphonates, alkylnaphthalenesulphonates, sulphates, ether sulphates and fatty alcohol sulphonates, quaternary ammonium salts such as trimethylcetylammonium bromide, cetylpyridinium bromide, optionally oxyethyleneated fatty acid ethanolamides, polyoxyethyleneated acids, alcohols or amines, polyglycerolated alcohols, polyoxyethyleneated or polyglycerolated alkylphenols, as well as polyoxyethyleneated alkyl sulphates.

The dyeing compositions are generally aqueous, but they may also contain organic solvents to solubilise compounds which would not be sufficiently soluble in water. Among these solvents, there may be mentioned by way of example, $C_2$–$C_4$ lower alkanols such as ethanol and isopropanol, glycerol, glycols or glycol ethers such as 2-butoxyethanol, ethylene glycol, propylene glycol, diethylene glycol monoethyl ether and monomethyl ether, as well as aromatic alcohols such as benzyl alcohol or phenoxyethanol, or mixtures of these solvents.

The composition applied to hair may also contain thickening agents chosen in particular from sodium alginate, gum arabic, cellulose derivatives such as methylcellulose, hydroxyethyl cellulose, hydroxypropyl cellulose, hydroxymethylcellulose, carboxymethylcellulose, optionally crosslinked acrylic acid polymers, xanthan gum. Inorganic thickening agents such as bentonite may also be used.

The composition may also contain antioxidants chosen in particular from sodium sulphite, thioglycolic acid, sodium bisulphite, ascorbic acid and hydroquinone, as well as other cosmetically acceptable adjuvants when the composition is intended to be used for dyeing human keratinous fibres, such as penetrating agents, sequestering agents, preservatives, buffers, perfumes and the like.

The composition applied to hair may be provided in various forms such as liquids, creams, gels or any other form suitable for dyeing hair. It may be packaged in an aerosol bottle in the presence of a propelling agent.

The subject of the invention is also the ready-for-use composition used in the process defined above.

According to a preferred embodiment, the process comprises a preliminary stage consisting in storing in separate form, on the one hand, the composition containing, in a medium suitable for dyeing, the coupler of formula (I) and the oxidation dye precursors in the form of a component (A) and, on the other hand, a composition containing the oxidising agent as defined above in the form of a component (B), and in mixing them immediately before applying this mixture to the keratinous fibres, as indicated above. Component (A) does not contain iodide ions in a sufficient amount to oxidise the coupler of formula (I).

The composition applied to keratinous fibres is obtained from a mixture of 10 to 90% of the component (A) with 90 to 10% of the component (B) containing an oxidising agent.

The subject of the invention is also an agent for dyeing keratinous fibres, in particular hair, essentially characterised in that it comprises at least two components, one of the components consisting of the component (A) defined above and the other consisting of the component (B) also defined above, the pH of the components (A) and (B) being such that after mixing in proportions of 90 to 10% for the component (A) and of 10 to 90% for the component (B), the resulting composition has a pH of less than 7.

In this embodiment, component (A), which contains at least one coupler of formula (I) and an oxidation dye precursor, has a pH of between 3 and 10.5 and may be adjusted to the chosen value by means of the alkalinising agents generally used in dyeing keratinous fibres, such as ammonium hydroxide, alkali metal carbonates, alkanolamines such as mono-, di- and triethanolamines as well as their derivatives, or conventional acidifying agents such as inorganic or organic acids such as hydrochloric acid, phosphoric acid, carboxylic acids such as tartaric acid or citric acid or sulphonic acids.

This composition may contain the various other adjuvants mentioned above, especially couplers different from the couplers of formula (I), excluding 2,4-diamino-1,3-dimethoxybenzene.

The range of para and/or ortho type oxidation dye precursors as well as the couplers are present in proportions preferably of between 0.3 and 7% by weight relative to the total weight of the component (A). The concentration of the coupler of formula (I) may vary between 0.05 and 3.5% by weight relative to the total weight of the component (A).

The surface-active agents are present in the component (A) in proportions of 0.1 to 55% by weight. When the medium contains solvents in addition to water, they may be present in proportions of between 0.5 and 40% by weight, and in particular between 5 and 30% by weight relative to the total weight of the component (A). The thickening agents are present preferably in proportions of between 0.1 and 5%, and in particular between 0.2 and 3% by weight. The antioxidants mentioned above are preferably present in the component (A) in proportions of between 0.02 and 1.5% by weight relative to the total weight of the component (A).

The component (B), containing the oxidising agent as defined above, has a pH of less than 7. This pH may have a minimum value of 1, and is preferably of between 1.5 and 3.5. This component (B) may be acidified with the same type of acidifying agents as those used for the component (A).

It may be provided in the form of a more or less thickened liquid, a milk or a gel.

This two-component dyeing agent may be packaged in a multi-compartment device or dyeing kit, or any other multi-compartment packaging system of which one contains the component (A) and the second contains the component (B); it being possible for these devices to be equipped with means enabling the desired mixture to be applied to the hair, such as the devices described in U.S. Pat. No. 4,823,985 by the Applicant.

The subject of the invention is also the use, as coupler, of an alkoxymetaphenylenediamine of formula (I) for dyeing keratinous fibres in acidic medium, in combination with oxidation dye precursors.

In conformity with the invention, the dyeing process consists in applying to the hair the mixture obtained, in allowing it to act for 3 to 40 minutes, and then in rinsing the hair and optionally shampooing it before another rinsing and drying.

It is also possible, in conformity with the invention, to apply separately a composition containing the coupler of formula (I), the oxidation dye precursor and the oxidising agent, so that the mixture which forms in situ on the fibres has a pH of less than 7, as defined above.

The following examples are intended to illustrate the invention without however being of a restrictive nature.

EXAMPLES 1 TO 23

The hair is dyed by applying to natural grey hair which is 90% white or to permanently waved grey hair, a freshly prepared mixture of the dyeing composition (A) and of the oxidising composition (B).

This mixture has the pH indicated in the table of examples below.

This mixture is allowed to act for 30 minutes, then the hair is rinsed and shampooed.

After drying, the hair is dyed in the shade specified at the bottom of the table.

|  | EXAMPLES | | | | |
|---|---|---|---|---|---|
| in g | 1 | 2 | 3 | 4 | 5 |
| A) Dyeing composition | | | | | |
| 2-Methoxymethyl-4-aminophenol | 0.46 | 0.46 | 0.46 | 0.46 | 0.46 |
| 2,4-Diaminoanisole dihydrochloride | 0.633 | | | | |
| 2-N-β-Hydroxyethylamino-4-amino-1,3,5-trimethoxy-benzene dihydrochloride | | 0.945 | | | |
| 2-N-β-Hydroxyethylamino-4-amino-1-methoxybenzene dihydrochloride | | | 0.765 | | |
| 4-N-β-Hydroxyethylamino-2-amino-1-methoxybenzene dihydrochloride | | | | 0.765 | |
| 2,4-Diamino-1,5-dimethoxy-benzene dihydrochloride, 1H$_2$O | | | | | 0.777 |
| Carrier | X | X | X | X | X |
| Water      gsp | 100 | 100 | 100 | 100 | 100 |
| B) Oxidising composition | | | | | |
| Solution of hydrogen peroxide at 20 volumes | | | | | |
| Phosphoric acid qs pH | 1.1 | 1.3 | 1.1 | 1.2 | 1.2 |
| pH = mixture w/w A + B | 6.7 | 6.6 | 6.7 | 6.6 | 6.7 |
| Shades obtained | | | | | |
| on natural grey hair which is 90% white | iridescent light blond | | light mahogany ash-iridescent | | ash iridescent |
| on permanently waved grey hair | | dark violet-red | | iridescent copper-coloured | |

| in g | 6 | 7 | 8 | 9 | 10 |
|---|---|---|---|---|---|
| A) Dyeing composition | | | | | |
| 2-Methoxymethyl-4-amino-phenol | 0.46 | 0.46 | 0.46 | 0.46 | 0.46 |
| 2,4-di-N-β-Hydroxyethyl-amino-1-methoxybenzene dihydrochloride | 0.898 | | | | |
| 2,4-Diamino-5-methoxy-phenoxyethanol dihydrochloride | | 0.814 | | | |
| 2,4-Diamino-1,3,5-tri-methoxybenzene dihydrochloride | | | 0.813 | | |
| 2,4-Diamino-1,5-di-β-hydroxy-ethoxybenzene dihydrochloride | | | | 0.904 | |
| 2,4-Diaminophenoxyethanol dihydrochloride | | | | | 0.723 |
| Carrier | X | X | X | X | X |
| Water      qsp | 100 | 100 | 100 | 100 | 100 |
| B) Oxidising composition | | | | | |
| Solution of hydrogen peroxide at 20 volumes | | | | | |
| Phosphoric acid qs pH | 1.4 | 1.3 | 1.1 | 1.3 | 1.4 |
| pH = mixture w/w A + B | 6.5 | 6.4 | 6.7 | 6.7 | 6.5 |

-continued

EXAMPLES

Shades obtained

| on natural grey hair which is 90% white | | | dark purple- light brown | | deep iridescent dark blond | | |
|---|---|---|---|---|---|---|---|
| on permanently waved grey hair | iridescent blond | | violet-red | | | copper coloured golden blond | |
| in g | 11 | 12 | 13 | 14 | 15 | 16 | 17 |
| A) Dyeing composition | | | | | | | |
| Para-phenylene-diamine | 0.324 | 0.324 | | | | | |
| 3-Methyl-4-amino-phenol | | | 0.369 | | | 0.369 | |
| Para-aminophenol | | | | 0.327 | 0.327 | | 0.327 |
| 2,4-Diamino-1,3,5-trimethoxybenzene dihydrochloride | 0.813 | | 0.813 | | 0.813 | | |
| 2-N-β-Hydroxy-ethylamino-4-amino-1,3,5-trimethoxybenzene dihydrochloride | | | | 0.945 | | 0.945 | |
| 2,4-di-N-β-hydroxyethylamino-1-methoxybenzene dihydrochloride | | 0.898 | | | | | 0.898 |
| Carrier | X | X | X | X | X | X | X |
| Water    qsp | 100 | 100 | 100 | 100 | 100 | 100 | 100 |
| B) Oxidising composition | | | | | | | |
| Solution of hydrogen peroxide at 20 volumes | | | | | | | |
| Phosphoric acid qs pH | 1.2 | 1.4 | 1.1 | 1.1 | 1.4 | 1.3 | 1.3 |
| pH = mixture w/w A + B | 6.6 | 6.5 | 6.5 | 6.6 | 6.5 | 6.6 | 6.6 |
| Shades obtained | | | | | | | |
| on natural grey hair which is 90% white | deep blue | | dark purple | dark purple- pink | | violet- pink | pink |
| on permanently waved grey hair | | dark purple | | | dark purple- red | | pink |

| in g | 18 | 19 | 20 | 21 | 22 | 23 |
|---|---|---|---|---|---|---|
| A) Dyeing composition | | | | | | |
| Paraphenylenediamine | | 0.327 | | 0.327 | | 0.327 |
| Para-aminophenol | | | 0.327 | | 0.327 | |
| 2,4-Diamino-6-methyl-1-methoxy-benzene dihydrochloride | 0.675 | 0.675 | | | | |
| 2,4-Diamino-1,6-dimethoxy-benzene dihydrochloride | | | 0.723 | 0.723 | | |
| 2,6-Diamino-4-methyl-1-methoxy-benzene dihydrochloride | | | | | 0.675 | 0.675 |
| Carrier | X | X | X | X | X | X |
| Water    qs | 100 | 100 | 100 | 100 | 100 | 100 |
| B) Oxidising composition | | | | | | |
| Solution of hydrogen peroxide at 20 volumes | | | | | | |
| Phosphoric acid qs pH | 1.2 | 1.4 | 1.1 | 1.4 | 1.3 | 1.3 |
| pH = mixture w/w A + B | 5.5 | 6.7 | 6.0 | 6.4 | 6.3 | 6.4 |
| Shades obtained | | | | | | |
| on natural grey hair which is 90% white | pink-beige | | | | | |
| on permanently waved grey hair | | light brown | night blue | pale deep purple | light auburn | golden light brown |

| FOUNDATION | |
|---|---|
| Polyglycerolated oleyl alcohol containing 2 mol of glycerol | 4.0 g |
| Polyglycerolated oleyl alcohol containing 4 mol of glycerol containing 78% of AI | 5.69 g AI |
| Oleic acid | 3.0 g |
| Oleylamine containing 2 mol of ethylene oxide, sold under the name ETHOMEEN 0 12 by the company AKZO | 7.0 g |
| Diethylaminopropyl laurylaminosuccinamate sodium salt containing 55% of AI | 3.0 g AI |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite in aqueous solution containing 35% of AI | 0.45 g AI |
| Ammonium acetate | 0.8 g |
| Antioxidant, sequestrant qs | |

I claim:

1. Process for dyeing keratinous fibres, consisting essentially of applying to the fibres a composition consisting essentially of, in a medium suitable for dyeing:

(1) as a coupler at least one alkoxymetaphenylenediamine of formula (I):

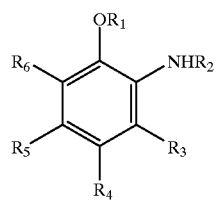

(I)

in which:

$R_1$ represents a $C_1$–$C_4$-alkyl radical, a $C_2$–$C_4$ mono- or polyhydroxyalkyl radical, a $C_1$–$C_4$-carboxyalkyl radical or a $C_1$–$C_4$-aminoalkyl radical whose amino group may be mono- or disubstituted by a $C_1$–$C_4$-alkyl;

$R_2$ represents a hydrogen atom, a $C_1$–$C_4$-alkyl radical, a $C_2$–$C_4$ mono- or polyhydroxyalkyl radical;

$R_3$ and $R_5$, independently of each other, represent H or OR, R denoting a $C_1$–$C_4$-alkyl radical or a $C_2$–$C_4$ mono- or polyhydroxyalkyl radical;

$R_4$ represents a hydrogen atom, a $C_1$–$C_4$-alkyl radical or NHR';

$R_6$ represents a hydrogen atom, a $C_1$–$C_4$-alkyl radical, OR or NHR', R having the meaning given above;

R' denotes a hydrogen atom, a $C_1$–$C_4$-alkyl radical or a $C_2$–$C_4$ mono- or polyhydroxyalkyl radical; provided that:

a) one of the radicals $R_4$ and $R_6$ denotes NHR' and the other of the radicals $R_4$ and $R_6$ does not denote NHR';

b) $R_3$ and $OR_1$ cannot simultaneously denote methoxy when $R_2$, $R_5$ and $R_6$ simultaneously denote hydrogen and $R_4$ a $NH_2$ group;

c) at least one of the radicals $R_3$, $R_4$, $R_5$ or $R_6$ denotes H;

d) $R_3$, $R_4$ and $R_5$ cannot simultaneously denote hydrogen when $R_6$ denotes $NH_2$, $R_2$ denotes hydrogen and $R_1$ denotes methyl;

e) when $R_1$ denotes ethyl and $R_2$, $R_3$, $R_5$ and $R_6$ denote hydrogen, $R_4$ cannot denote $NH_2$;

f) $R_4$ must represent NHR' when $R_1$ denotes carboxyalkyl or aminoalkyl;

g) if $R_4$ represents NHR', R' cannot denote a $C_2$–$C_4$ mono- or polyhydroxyalkyl radical;

or salts of these compounds;

(2) at least one oxidation dye precursor or oxidation base; and (3) at least one oxidizing agent;

the pH of the composition applied to the fibres being less than 7.

2. Process according to claim 1, wherein the coupler of formula (I) is chosen from:

2,4-diaminoanisole,

2-N-β-hydroxyethylamino-4-amino-1,3,5-trimethoxybenzene,

2-N-β-hydroxyethylanino-4-amino-1-methoxybenzene, 2,4-diamino-1,5-dimethoxybenzene, 2,4-diamino-5-methoxyphenoxyethanol, 2,4-diamino-1,3,5-trimethoxybenzene, 2,4-diamino-1,5-di-(β-hydroxyethoxy)benzene, 2,4-diaminophenoxyethanol, 2,4-diamino-6-methyl-1-methoxybenzene, 2,4-diamino-1,6-dimethoxybenzene, 2,6-diamino-4-methyl-1-methoxybenzene, or their salts.

3. Process according to claim 1, wherein the oxidation dye precursor is a para-phenylenediamine, para-aminophenol or para-heterocyclic precursor.

4. Process according to claim 3, wherein the para-phenylenediamine is a compound of formula:

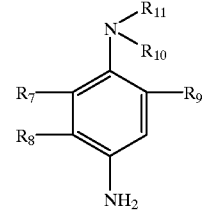

(II)

in which:

$R_7$, $R_8$ and $R_9$, which are identical or different, represent a hydrogen or halogen atom, an alkyl radical having 1 to 4 carbon atoms, an alkoxy radical having 1 to 4 carbon atoms;

$R_{10}$ and $R_{11}$, which are identical or different, represent a hydrogen atom, an alkyl, hydroxyalkyl, alkoxyalkyl, carbamylalkyl, mesylaminoalkyl, acetylaminoalkyl, ureidoalkyl, carbalkoxyaminoalkyl, sulphoalkyl, piperidinoalkyl or morpholinoalkyl radical; these alkyl or alkoxy groups having 1 to 4 carbon atoms, or alternatively $R_{10}$ and $R_{11}$ form, together with the nitrogen atom to which they are attached, a piperidino or morpholino heterocycle, provided that $R_7$ or $R_9$ represents a hydrogen atom when $R_{10}$ and $R_{11}$ do not represent a hydrogen atom, or salts of these compounds excluding 2,6-dimethylparaphenylenediamine and 2,3-dimethylparaphenylenediamine.

5. Process according to claim 4, wherein the compound of formula (II) is isopropyl-p-phenylenediamine, p-phenylenediamine, 2-methyl-p-phenylenediamine, methoxyparaphenylenediamine, chloroparaphenylenediamine, 2-methyl-5-methoxyparaphenylenediamine, 2,6-dimethyl-5-methoxyparaphenylenediamine,N,N-dimethylparaphenylenediamine, 3-methyl-4-amino-N,N-diethylaniline, N,N-di-(β-hydroxyethyl) paraphenylenediamine, 3-methyl-4-amino-N,N-di-(β-hydroxyethyl)aniline, 3-chloro-4-amino-N,N-di-(β-hydroxyethyl)aniline, 4-amino-N,N-(ethylcarbamylmethyl) aniline, 3-methyl-4-amino-N,N-(ethylcarbamylmethyl) aniline, 4-amino-N,N-(ethyl-β-piperidinoethyl)aniline, 3-methyl-4-amino-N,N-(ethyl-β-piperidinoethyl)aniline, 4-amino-N,N-(ethyl-β-morpholinoethyl)aniline, 3-methyl-4-amino-N,N-(ethyl-β-morpholinoethyl)aniline, 4-amino-N,N-(ethyl-β-acetylaminoethyl)aniline, 4-amino-N-(β-methoxyethyl)aniline, 3-methyl-4-amino-N,N-(ethyl-β-acetylaminoethyl)aniline, 4-amino-N,N-(ethyl-β-mesylaminoethyl)aniline, 3-methyl-4-amino-N,N-(ethyl-β-mesylamino-ethyl)aniline, 4-amino-N,N-(ethyl-β-sulphoethyl)aniline, 3-methyl-4-amino-N,N-(ethyl-β-sulphoethyl)aniline, N-((4'-amino-)phenyl)-morpholine or N-((4'-amino)phenyl)piperidine or salts thereof.

6. Process according to claim 3, wherein the p-aminophenol is chosen from p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2-hydroxymethyl-4-aminophenol, 2-(β-hydroxyethyl)-4-aminophenol, 2-methoxy-4-aminophenol, 3-methoxy-4-aminophenol, 2,5-dimethyl-4-aminophenol, 2-methoxymethyl-4-aminophenol, 2-aminomethyl-4-aminophenol, 2-β-hydroxyethylaminomethyl-4-aminophenol, 2-ethoxymethyl-4-aminophenol, 2-(β-hydroxyethoxy)methyl-4-aminophenol, N-(2-hydroxy-5-aminobenzyl)-2-methoxyethylamine, N-(2-hydroxy-5-aminobenzyl)-1-methoxyisopropylamine, N-(2-hydroxy-5-aminobenzyl)-3-isopropoxypropylamine, 2-acetylamino-4-aminophenol or 5-aminosalicylic acid.

7. Process according to claim 1 wherein the oxidation dye precursor is ortho-aminophenol or ortho-phenylenediamine.

8. Process according to claim 1, wherein the oxidising agent is hydrogen peroxide, urea peroxide, alkali metal bromates or persalts.

9. Process according to claim 1, wherein the pH of the composition applied to the keratinous fibres is between 3 and 6.9.

10. Process according to claim 1, wherein the composition for dyeing keratinous fibres consists essentially of, in addition to the coupler of formula (I), other couplers which are meta-diphenols, meta-aminophenols, meta-phenylenediamines, meta-N-acylaminophenols, meta-ureidophenols, meta-carbalkoxyaminophenols, α-naphthol, indole couplers, or couplers possessing an active methylene group which are diketonic compounds or pyrazolones, excluding 2,4-diamino-1,3-dimethoxybenzene.

11. Process according to claim 10, wherein the couplers are chosen from 2,4-dihydroxyphenoxyethanol, 2,4-dihydroxyanisole, meta-aminophenol, resorcinol, resorcinol monomethyl ether, 2-methylresorcinol, pyrocatechol, 2-methyl-5-N-(β-hydroxyethyl)aminophenol, 2-methyl-5-N-(β-mesylaminoethyl)aminophenol, 6-hydroxybenzomorpholine, 6-aminobenzomorpholine, 2-methyl-5-aminophenol, 2,6-dimethyl-3-aminophenol, 3,4-methylenedioxyphenol, 3,4-methylenedioxyaniline, 4-hydroxyindole, 6-hydroxyindole, 7-hydroxyindole, 7-aminoindole or their salts.

12. Process according to claim 1, wherein the composition further consists essentially of anionic, cationic, nonionic or amphoteric surface-active agents or mixtures thereof; thickening agents, or antioxidants.

13. Process according to claim 1, wherein the medium suitable for dyeing consists of water or a mixture of water and a solvent which is $C_2$–$C_4$ lower alkanols, glycerol, glycols or glycol ethers, diethylene glycol monoethyl ether or monomethyl ether, aromatic alcohols or mixtures thereof.

14. Agent for dyeing keratinous fibres consisting essentially of at least two components; one component (A) consisting essentially of, in a medium suitable for dyeing, as a coupler at least one alkoxymetaphenylenediamine of formula (I):

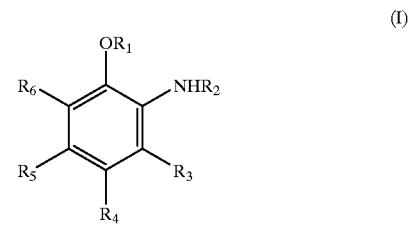

in which:
R$_1$ represents a $C_1$–$C_4$ alkyl radical, a $C_2$–$C_4$ mono- or polyhydroxyalkyl radical, a $C_1$–$C_4$-carboxyalkyl radical or a $C_1$–$C_4$-aminoalkyl radical whose amino group may be mono- or disubstituted by a $C_1$–$C_4$-alkyl;
R$_2$ represents a hydrogen atom, a $C_1$–$C_4$-alkyl radical, a $C_2$–$C_4$ mono- or polyhydroxyalkyl radical;
R$_3$ and R$_5$, independently of each other, represent H or OR, R denoting a $C_1$–$C_4$-alkyl radical or a $C_2$–$C_4$ mono- or polyhydroxyalkyl radical;
R$_4$ represents a hydrogen atom, a $C_1$–$C_4$-alkyl radical or NHR';
R$_6$ represents a hydrogen atom, a $C_1$–$C_4$-alkyl radical, OR or NHR', R having the meaning given above;
R' denotes a hydrogen atom, a $C_1$–$C_4$-alkyl radical or a $C_2$–$C_4$ mono- or polyhydroxyalkyl radical; provided that:
a) one of the radicals R$_4$ and R$_6$ denotes NHR' and the other of the radicals R$_4$ and R$_6$ does not denote NHR';
b) R$_3$ and OR$_1$ cannot simultaneously denote methoxy when R$_2$, R$_5$ and R$_6$ simultaneously denote hydrogen and R$_4$ a NH$_2$ group;
c) at least one of the radicals R$_3$, R$_4$, R$_5$ or R$_6$ denotes H;
d) R$_3$, R$_4$ and R$_5$ cannot simultaneously denote hydrogen when R$_6$ denotes NH$_2$, R$_2$ denotes hydrogen and R$_1$ denotes methyl;
e) when R$_1$ denotes ethyl and R$_2$, R$_3$, R$_5$ and R$_6$ denote hydrogen, R$_4$ cannot denote NH$_2$;
f) R$_4$ must represent NHR' when R$_1$ denotes carboxyalkyl or aminoalkyl;
g) if R$_4$ represents NHR', R' cannot denote a $C_2$–$C_4$ mono- or polyhydroxyalkyl radical;
or salts of these compounds;
and an oxidation dye precursor in an effective amount to form a dye by oxidative condensation which is a para-phenylenediamine, a para-aminophenol or a para-heterocyclic precursor, the at least one alkoxymetaphenylenediamine being present in component (A) in an effective amount to vary the shade of the dye and a component (B) consisting essentially of, in a medium suitable for dyeing, an oxidizing agent in an effective amount to oxidize the oxidation dye precursor by oxidative condensation, the pH of the components (A) and (B) being such that after mixing in proportions of 90 to 10% for the component (A) and 10 to 90% for the component (B), the resulting composition has a pH of less than 7.

15. Agent according to claim 14, wherein the component (A) has a pH of between 3 and 10.5.

16. Agent according to claim 14, wherein the component (A) consists essentially of para oxidation dye precursors or mixtures thereof and the coupler, in proportions of between 0.3 and 7% by weight relative to the total weight of the component (A).

17. Agent according to claim 14, wherein the concentration of the coupler of formula (I) is between 0.05 and 3.5% by weight relative to the total weight of the component (A).

18. Agent according to claim 14, wherein the component (A) further consists essentially of surface-active agents in proportions of 0.1 to 55% by weight, solvent agents, in proportions of between 0.5 and 40% by weight, thickening agents in proportions of between 0.1 and 5% by weight, or antioxidants in proportions of between 0.02 and 1.5% by weight.

19. Agent according to claim 14, wherein the component (B) has a pH which has a minimum value of 1 and a value of less than 7.

20. Process for dyeing keratinous fibres, consisting essentially of a first storing, in separate form, the components of the dyeing agent as defined in claim 14, and in mixing, before application, the components (A) and (B) in proportions of 10 to 90% for the component (A), and 90 to 10% for the component (B), so as to obtain a composition having a pH of less than 7 and then applying this mixture to the keratinous fibres immediately after preparation.

21. Multi-compartment device or dyeing kit, consisting essentially of at least two compartments, of which a first compartment consists essentially of the component (A) as defined in claim 14, and the second compartment consists essentially of the component (B) as defined in claim 14.

22. Device according to claim 21, further consisting essentially of means which make it possible to apply to hair a mixture of the components (A) and (B) as defined in claim 14.

23. Dyeing process according to claim 1, wherein the composition is applied to hair for 3 to 40 minutes, the hair is rinsed and optionally shampooed before another rinsing and drying.

24. Process according to claim 1, wherein the oxidizing agent is hydrogen peroxide.

25. Agent according to claim 14, wherein the oxidizing agent is hydrogen peroxide.

* * * * *